United States Patent [19]

Nagai et al.

[11] Patent Number: 4,717,716

[45] Date of Patent: Jan. 5, 1988

[54] IMMUNO-REGULATOR

[75] Inventors: Kineshiro Nagai, Tokyo; Taiko Suda, Kashiwa, both of Japan

[73] Assignee: Nihon University, Tokyo, Japan

[21] Appl. No.: 792,157

[22] Filed: Oct. 28, 1985

[30] Foreign Application Priority Data

Feb. 13, 1985 [JP] Japan .................................. 60-25494

[51] Int. Cl.⁴ ............................................. A61K 37/02
[52] U.S. Cl. ...................................... 514/19; 514/885; 548/344
[58] Field of Search ............... 514/19, 885; 260/998.2; 548/344

[56] References Cited

U.S. PATENT DOCUMENTS 4,446,149  5/1984  Nagai ..................................... 514/19

Primary Examiner—Delbert R. Phillips
Assistant Examiner—Nathan M. Nutter
Attorney, Agent, or Firm—Browdy and Neimark

[57] ABSTRACT

An immuno-regulator for recovering immuno-reaction from its abnormal fall and suppressing its excessive acceleration in order to maintain normal function is disclosed, which contains L-carnosine or its salt as an effective ingredient.

7 Claims, No Drawings

IMMUNO-REGULATOR

FIELD OF THE INVENTION

This invention relates to an immuno-regulator containing L-carnosine or its salt as an effective ingredient.

BACKGROUND OF THE INVENTION

In order to treat various diseases caused by abnormal function of immunity, various pharmaceutical agents, which are generally referred to as immuno-regulators, have been developed. The term "immuno-regulator" as used herein signifies agents for recovering immunoreaction from its abnormal fall and suppressing its excessive acceleration in order to maintain normal function of immunity. As the agents belonging to such category, there have been developed various types of agents including levamisol (Aldrich Corporation). However, these conventional immuno-regulators are derived from chemical materials but not from biological materials, so that their dangerous side-effects can not be completely eliminated. In fact, significant side effects have been reported for some immuno-regulators.

Essentially the immuno-reaction has physiological function for maintaining homeostasis, which is supposed to be regulated by physiologically active substances contained in a living body.

Accordingly, an object of the invention is to provide an immuno-regulator of physiologically active substance having less side effects in lieu of conventional chemical substances.

SUMMARY OF THE INVENTION

In view of the foregoing, the invention provides an immuno-regulator containing L-carnosine or its salt as an effective ingredient.

DETAILED DESCRIPTION OF THE INVENTION

It has now been found out by studying for many years physiological action of ω-amino acids contained in a living body that L-carnosine, which is a physiologically active derivative, has an immuno-regulatory function. There has not hitherto been found any physiologically active agent having such immuno-regulatory function. Further, it has not been known that L-carnosine has the immuno-regulatory function.

L-carnosine, or β-alanyl-L-histidine was discovered in a Liebig's meat extract by Gulewitsh in 1900, and is a dipeptide consisting of L-histidine and β-alanine, which is contained abundantly in mammal skeletal muscles. Since discovery of L-carnosine, its physiological significane and pharmacological utility have been studied by many researchers but yet remain unsolved.

L-carnosine is in the form of tasteless, odorless, readily water-soluble and white crystalline powder having a melting point of 250° C. and $[\alpha]_D^{20} = +20.0$ (H$_2$O). It has the following structural formula:

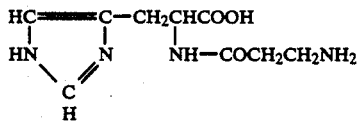

and its pH in an aqueous solution is in the range of 8.0 to 8.5.

L-carnosine is a substance contained abundantly in various mammal skeletal muscles (about 0.1–0.3) and is usually taken from meat foods as a supplying source for an essential amino acid L-histidine. Further, it may be biosynthesized from L-histidine and β-alanine. L-carnosine, which has been absorbed, is decomposed by carnosinase into nutritious L-histidine and β-alanine, a portion of which is re-synthesized into L-carnosine[β-alanyl-1-methyl-histidine (anserine) is known as an intermediate of the L-carnosine biosynthesis].

As described hereinabove, L-carnosine is a food-like substance of high safety and may be decomposed, after absorption, by carnosinase contained in various internal organs, and thus is quite different from many other pharmaceuticals which are metabolized in a liver and impose heavy burden to hepatic function.

Acute toxicity of L-carnosine will be demonstrated hereinbelow.

Acute Toxity

L-carnosine was administered peritoneally or orally in different amounts to a group of 10 mice and acute toxic symptoms were observed 5 hours after administration. LD50 was calculated from the death number after 75 hours according to a Vander Waerden method. L-carnosine was dissolved in a physiological saline so as to give a dose of 0.1 to 0.3 ml/10 g.

The following toxic symptoms of L-carnosine were observed. From about 30 minutes after peritoneal administration of 15,000 mg/Kg (LD 100), a half of the mice showed depression of voluntary motility, abdominal position, depression and irregularity of respiration rate, absence of disappearance in righting and escaping reflexes, tail-raising reaction, and myoclonia. Further progressive symptoms result in repetitious lateral turnigs, reflex acceleration on contact stimulation, conculsions, and finally tonic cramp to death. 50%, 80% and 100% of mice died on 30 minutes, 2 hours and 5 hours, respectively. Oral administration of 15,000 mg/Kg showed little effect, but killed one of the 10 treated mice after 12 hours.

TABLE 1

| | LD50 of L-carnosine |
|---|---|
| Route | LD50 (95% confidence limit) mg/Kg |
| Peritoneal | 9,087 (8,320–9,925) |
| Oral | >14,930 (minimal lethal dose) |

The acute toxicity (value on 72 hours) to DDY male mouse is shown in the table. As shown, L-carnosine is a compound of very low toxicity.

Since 10 years ago, L-carnosine has been formulated as an anorexia treating agent by LISA corporation in Spain and confirmed to be safe. Further, an effective amount of L-carnosine to transplantable tumors is 1 mg per mouse, or 50 mg/Kg. This amount corresponds to 1/181 of the acute toxicity LD50 (9,087 mg/Kg) in the peritoneal administration, and thus suggests high safety of L-carnosine.

A synthetic method of L-carnosine is known [Journal of Biological Chemistry, 108, 753 (1935)]. L-carnosine may be prepared by chlorinating carbobenzoxy-β-alanine with phosphorus pentachloride, forming its methyl ester with methanol, forming azide through hydroazide, coupling the azide with L-histidine methyl ester and finally removing the carbobenzoxy group by means of catalytic reduction. The invention includes a treating agent containing a salt of L-carnosine, such as salts on its carboxyl group, acid adducts with pharmaceutically acceptable acids on its amino group and salts on both carboxyl and amino groups. As the salts on the carboxyl group, there may be mentioned salts with metal, such as sodium, potassium, calcium, magnesium, zinc and aluminium, as well as substituted ammonium salts, such as salts with trialkylamines (for example, triethylamine) and other amines. As the salts on the amino group, there may be mentioned salts with organic and inorganic acids, such as hydrochloric, sulfonic, phosphoric, acetic, propionic, lactic, tartaric, citric, succinic, maleic, benzene-sulfonic and toluenesulfonic acids. These salts may be prepared in a known method by reaction of free L-carnosine with a stoichiometric amount of selected acid or base.

The significant immuno-regulatory effect of L-carnosine will be described with reference to experimental examples.

Experimental Method

The immuno-regulatory effect was evaluated by a hemolytic plague method (PEC), a hemagglutination test and a delayed hypersensitivity reaction, using mice.

(1) PFC Method

Antibody-producing capacity was evaluated by counting plague-forming cells by means of a modified Canningham method, or a liquid chamber-slide method [Hashimoto et al., Experimental Method for Immunity A, p 491–494 (1972), edited by Japan Immunology Academy]. For sensitization, sheep red blood cells (SRBC, supplied by Shizuoka Experimental Animal Corporation) were utilized, which were in principle diluted with phosphate buffered saline, PBS) to prepare a solution containing $12.5 \times 10^8$ SBRC/ml, 0.2 ml ($2.5 \times 10^8$ cells) of which was injected into a tail vein of a DDY mouse (male, 5 weeks age, available from Shizuoka Experimental Animal Corporation). As a reaction medium, an Eagle MEM medium containing 10% bovine fetal serum (FCS) (supplied by Nissui Pharmaceutical Co., Ltd.) was used, to which were mixed 0.1 ml of $4 \times 10^7$ splenic cells/ml soltuion, 0.5 ml of $2.5 \times 10^9$ SRBC/ml solution ($12.5 \times 10^8$ cells) and 0.4 ml of $\frac{1}{4}$ diluted complemental serum of a guinea pig to prepare a mixed solution which was then sealed in a chamber and warmed at 37° C. for one hour. According to this method, 50–150 PFC cells were detected in about 0.02 ml chamber.

(2) Determination of Serum Antibody Value

Blood was collected in the PFC reaction from carotid arteries of a group of five mice, from which was separated a serum in a conventional manner for determination of hemagglutination titer (HA-titer). The test serum was diluted with a phosphate buffered saline (PBS) containing 0.5–1% of a serum from a normal rabbit, and was evaluated using SRBC. The maximal dilution showing positive reaction was represented by $2^N$, wherein N represents an antibody value.

(3) Delayed Hypersensitivity Reaction

[Natsuume et al., Experimental Method of Immunity A, p 614–620 (1972), Japan Immunology Academy].

A male DDY mouse of 5 weeks are weighing about 20 g was used to detect its contact dermatitis by means of 2, 4, 6-trinitro-chlorobenzene (picryl chloride) (available from Tokyo Chemical Industry Co., Ltd). An ethanol solution of 1% picryl chloride was impregnated into 4-layered gauge ($1 \times 1$ cm), which was then contacted with a shaved abdomen of the mouse for 10 seconds to cause primary sensitization. The secondary sensitization for test was caused on seventh day by applying an olive oil solution of 1% picryl chloride on both surfaces of one ear by means of a paint brush. The other ear had applied only olive oil as a control. After 24 hours, the mouse was anesthetized with ether, and thickness of the ear was determined in the order of 1/100 mm by a micrometer having precision of 1/100 mm. The delayed hypersensitivity reaction was calculated as follows: (Thickness of Ear Applied with Picryl Chloride after 24 Hours—Thickness of Ear before Application) minus (Thickness of Ear Applied with Olive Oil After 24 Hours—Thickness of Ear before Application).

(4) Experiments for the immuno-regulatory effect of L-carnosine were carried out by varying an amount of antigen, a dose of L-carnosine and an animal age, on the standard of an antigen amount of $2.5 \times 10^8$ SRBC and a mouse of 5 weeks age, in the following condition:

(a) Variation of Antigen Amount

Sensitizing antigen amounts ranging from $5 \times 10^7$ to $2.5 \times 10^9$ SRBC were used for observing the effect of 100 mg/Kg dose of L-carnosine.

(b) Variation of Mouse Age

Mice ranging from an immature mouse of 2 weeks age to an old mouse of more than 30 weeks age were used for observing the effect of 100 mg/Kg dose of L-carnosine.

(c) Variation of L-carnosine was varied to observe the effect on PFC reaction, hemagglutination reaction and delayed hypersensitivity reaction.

EXPERIMENTAL RESULTS

Experimental results are shown Tables below.

TABLE 2

Effect of L-carnosine on PFC Reaction And Hemagglutination reaction (HA-titer) of A Mouse Immunized with Varied Dose of SRBC

| SRBC Antigen Amount | | PFC Number (%) | | | | Anti-SRBC Antibody Value N*** |
|---|---|---|---|---|---|---|
| | | per Chamber | per Spleen | Weight of Spleen (g) | per g. Spleen | |
| $5 \times 10^7$ | Normal | $30.2 \pm 2.9$ (100) | $5.1 \times 10^4$ (100) | 0.12 (100) | $4.2 \times 10^5$ (100) | 3 |
| | L-carnosine* | $39.4 \pm 3.8$ (130) | $6.9 \times 10^4$ (135) | 0.14 (117)' | $5.0 \times 10^5$ (119) | 4 |
| $5 \times 10^8$ | Normal | $93.2 \pm 2.9$ (100) | $18.6 \times 10^4$ (100) | 0.12 (100) | $15.5 \times 10^5$ (100) | 9 |
| | L-carnosine** | $67.1 \pm 4.8$ (72) | $12.2 \times 10^4$ (66) | 0.15 (125) | $8.2 \times 10^5$ (53) | 7 |
| $2.5 \times 10^9$ | Normal | $124.3 \pm 3.6$ (100) | $24.9 \times 10^4$ (100) | 0.17 (100) | $14.3 \times 10^5$ (100) | 10 |

TABLE 2-continued

Effect of L-carnosine on PFC Reaction And
Hemagglutination reaction (HA-titer) of
A Mouse Immunized with Varied Dose of SRBC

| SRBC Antigen Amount | PFC Number (%) | | | | Anti-SRBC Antibody Value N*** |
|---|---|---|---|---|---|
| | per Chamber | per Spleen | Weight of Spleen (g) | per g. Spleen | |
| L-carnosine*** | 86.3 ± 5.5 (69) | $21.1 \times 10^4$ (85) | 0.21 (124) | $10.2 \times 10^5$ (71) | 8 |

To a group of mice administered with L-carnosine (100 mg/Kg/day S.C.) for six days and to a group of normal mice were injected sheep red blood cells (SRBC) through their tail veins for immunization, and after four days the PFC reaction was conducted. Values are shown in an average of five mice ± S.D.

*$P < 0.01$
**$P < 0.001$ control group
***Blood was collected upon the PFC reaction, from which was separated serum on the next day for the agglutination test. For the antibody value (N) the maximal dilution showing positive reaction is represented by $2^N$, wherein N represents the antibody value.

TABLE 3

Effect of L-carnosine on PFC Reaction And
Hemagglutination Reaction (HA-titer) in
Mice of Varied Ages Immunized with SRBC

| Week Age | L-carnosine | PFC Number (%) | | | | Anti-SRBC Antibody Value N** |
|---|---|---|---|---|---|---|
| | | per Chamber | per Spleen | Weight of Spleen (g) | per g. Spleen | |
| 2 | — | 69.7 ± 5.9 (100) | $11.2 \times 10^4$ (100) | 0.15 (100) | $7.5 \times 10^5$ (100) | 9–10 |
| | +* | 50.8 ± 1.9 (73) | $6.7 \times 10^4$ (60) | 0.14 (93) | $4.8 \times 10^5$ (64) | 6–7 ↓ |
| 5 | — | 79.7 ± 8.8 (100) | $17.1 \times 10^4$ (100) | 0.15 (100) | $11.4 \times 10^5$ (100) | 9–10 |
| | + | 85.3 ± 7.2 (107) | $18.8 \times 10^4$ (110) | 0.15 (100) | $12.5 \times 10^5$ (110) | 9–10 → |
| 30 | — | 40.4 ± 2.5 (100) | $12.6 \times 10^4$ (100) | 0.19 (100) | $6.6 \times 10^5$ (100) | 4–5 |
| | +* | 82.5 ± 4.4 (204) | $26.8 \times 10^4$ (213) | 0.23 (121) | $11.7 \times 10^5$ (177) | 9 ↑ |

To a group of mice administered with L-carnosine (100 mg/Kg/day S.C.) for 9 days and to a group of normal mice were injected $2.5 \times 10^8$ sheep red blood cells (SRBC) through their tail veins for immunization, and after 4 days the PFC reaction was conducted. Values are shown in an average of 5 mice ± S.D.

*$P < 0.001$ control group
**Blood was collected upon the PFC reaction, from which was separated serum on the next day for the agglutination test. For the antibody value (N) the maximal dilution showing positive reaction is represented by $2^N$, wherein N represents the antibody value.

TABLE 4

Effect of Varied Amount of L-carnosine on
PFC Reaction And Hemagglutination Reaction
(HA-titer) of Mice Immunized with SRBC

| Amount of L-Carnosine | PFC Number (%) | | | | Anti-SRBC Antibody Value N** |
|---|---|---|---|---|---|
| | per Chamber | per Spleen | Weight of Spleen (g) | per g. Spleen | |
| 0 mg/kg | 60.3 ± 8.9 (100) | $8.7 \times 10^4$ (100) | 0.15 (100) | $5.7 \times 10^5$ (100) | 8 |
| 25 mg/kg | 53.0 ± 6.1 (88) | $10.7 \times 10^4$ (123) | 0.14 (92) | $7.6 \times 10^5$ (133) | 9 ↑ |
| 50 mg/kg* | 73.6 ± 6.2 (122) | $14.9 \times 10^4$ (171) | 0.18 (116) | $8.5 \times 10^5$ (149) | 10 ↑ |
| 250 mg/kg** | 69.8 ± 6.5 (116) | $14.6 \times 10^4$ (168) | 0.15 (100) | $9.5 \times 10^5$ (167) | 9 ↑ |
| 500 mg/kg | 64.8 ± 4.9 (107) | $8.3 \times 10^4$ (95) | 0.14 (89) | $6.1 \times 10^5$ (107) | 8 → |

To a group of mice administered with L-carnosine for 6 days and to a group of normal mice were injected $2.5 \times 10^8$ sheep red blood cells (SRBC) through their tail veins for immunization, and after 4 days the PFC reaction was conducted. Values are shown in an average of 5 mice ± S.D.

*$P < 0.01$
**$P < 0.05$ control group
***Blood was collected upon the PFC reaction, from which was separated serum on the next day for the agglutination test. For the antibody value (N) the maximal dilution showing positive reaction is represented by $2^N$, wherein N represents the antibody value.

TABLE 5

Effective of Varied Amounts of L-carnosine on Delayed Hypersensitivity Reaction (DHR) of Mice

| Amount of L-carnosine (mg/kg/day) | Thickness × $10^{-3}cm$ | Increase of Ear control % |
|---|---|---|
| 0 | 11.5 ± 4.0 | (100) |
| 50 | 14.1 ± 3.6 | 122.6 |
| 250 | 15.7 ± 2.5* | 136.5 |
| 500 | 21.3 ± 8.7* | 185.2 |

*$P < 0.05$ control group

L-carnosine was administered subcutaneously in the indicated amount for 14 days. On the 7th day, sensitization was conducted by 1% picryl chloride, and examination was carried out on 7 days later. Values are shown in an average of 8 mices ±S.D.

Study of Experimental Results

1. Effects on PFC Reaction And Hemagglutination Reaction (HA-titer) of A Mature Mouse in Case of Varied Dose of Antigen.

A test method therefor is a standard method for screening immuno-regulatory substances. Under a conditioin of using a less amount of antigen to keep as low response of antibody in a normal spleen of an animal the reaction is strengthened, whereas in case of using a larger amount of antigen to increase the response the reaction is suppressed. After 100 mg/Kg of L-carnosine was administered for 6 days, the sensitization was conducted with $5 \times 10^7$ cells, $5 \times 10^8$ cells or $2.5 \times 10^9$ cells of SRBC. The PFC reaction and the hemagglutination reaction after 4 days were shown in Table 2. In the normal group the PFC was increased proportionally to the antigen amount, while in the L-carnosine dosage group the PFC was increased 30% for the small antigen amount ($5 \times 10^7$ SRBC) and decreased 30% for the large antigen amount ($5 \times 10^8$, $2.5 \times 10^9$ SRBC). This results may be supported by the hemagglutination reaction to the SRBC, in which the reaction was not altered for $5 \times 10^8$ SRBC, but was increased from 3 up to 4 for $5 \times 10^7$ SRBC and decreased from 10 down to 8 for $2.5 \times 10^9$ SRBC.

2. Effects on PFC Reaction And Hemagglutination Reaction in Case of Varied Age of A Mouse An immature mouse showed generally a higher immuno-response than a mature mouse, and the immuno-response decreased with increase of the mouse age. Table 3 shows the results of comparison, in which the mice of 2, 5 and 30 weeks age each administered with 100 mg/Kg of L-carnosine for 9 days were compared with the normal mouse. No effect on the PFC response was observed for the mature mouse of 5 weeks age but the immuno-response was suppressed for the immature mouse of 2 weeks age, whereas the low PFC response was doubly strengthened for the old mouse of 30 weeks age. These results were also supported by the hemagglutination reaction.

3. Effects on Immuno-Response by Varied Dose of L-Carnosine

As described hereinbefore, L-carnosine has the immuno-regulatory action but is known to be used in an optimum dose for generating an action of the immuno-regulator, which shows an inhibitory phenomenon when applied in an excessive amount over a certain level and is different from other medicaments showing proportional relation between the dosage level and the effect. This mechanism is not yet known, and has been studied for L-carnosine. The PFC reaction for the mouse of 5 weeks age in the level of $2.5 \times 10^8$ SRBC was increased by the dose of 50 and 250 mg/Kg for 6 days, but subsided by the dose of more than 500 mg/Kg. The hemagglutination reaction also subsided in the level of more than 500 mg/Kg (Table 4). The DHR with 1% picryl chloride shows an increasing trend of reaction, depending on the doses of 50, 250 and 500 mg/Kg (Table 5). By the fact that the DHR is increased, L-carnosine is confirmed to have the immuno-regulatory action.

Presumable Clinical Application

From the animal experimental results in the hemolytic plaque method (PFC) and the delayed hypersensitivity reaction (DHR), it will be appreciated that the optimum dosage for the immuno-regulatory action is 100 mg/Kg/day of L-carnosine (subcutaneous route), from which the dose of 5 g/day is calculated for the adult having a body weight of 50 Kg. The constituents of L-carnosine are β-alanine and L-histidine which are amino acids in vivo. Thus, L-carnosine is a highly safe immuno-regulator which may be used without danger of side-effects.

Immuno-Diseases to be Clinically Applied

L-carnosine is used non-specifically to diseases caused by immuno-abnormality. There may be mentioned the following diseases, for example:

serum disease, lupus erythematosus, various types of rheumatism, mixed clioglobulinemia, mixed connective tissue disease, HBV (hepatic virus B-type) antigen-antibody complex disease, immunoblast lymphadenitis, scleroderma, mesenchyma ataxic syndrome, serious myasthenia, Hashimoto's disease, Basedow's disease, asmyloidosis, Behcet's syndrome, immuno-insufficience syndrome, Hodgkin's disease, multiple sclerosis, organ-specific auto-immune disease and others.

L-carnosine seems very suitable as an immuno-regulatory substance for transplantation of organs.

The immuno-regulator according to the invention, as described hereinabove, may be in any form which enables L-carnosine to be administered conveniently through oral or parenteral route, such as injectable solutions, powders, granules, tablets, capsules, enteric coatings, inhalation agents, troches, ointments and others. These agents may be administered individually or in combination thereof, depending on symptoms. A dose may be varied in a wide range, depending on routes of dosage, types and forms of the agent, and symptoms. As examples, typical forms, doses and routes for the medicament according to the invention are shown in the following.

| Form | Dose and Route |
|---|---|
| Inject. Solution | 5% solution, 0.1–1.0 ml at each time, local injection |
| Ointment | 1% ointment, 1 g at each time, local application |

The doses and routes are shown merely for illustrative purpose and may be optionally varied in a wide range, depending on symptoms of patients, due to high safety of L-carnosine.

L-carnosine is readily soluble in water, so that its 0.3%, 0.5% or 1.0% isotonic solution may be readily prepared by aseptic operation. The isotonic solution may be sealed in an ampoule under an inert gas for injection through a conventional syringe. Alternatively, L-carnosine powder, which has previously been lyophilized and sealed in an ampoule or vial by aseptic operation, may be dissolved to prepare 0.3%, 0.5% or 1.0% isotonic solution immediately before injection.

Powders, granules, tablets or capsules for oral dosage may be prepared in conventional methods well known in the art using binders, such as syrupy arabic gum, gelatin, sorbitol, tragacanth or polyvinyl pyrolidone; excipients, such as lactose, corn starch, calcium phosphate, sorbitol or glycine; lubricants, such as magnesium stearate, talc, polyethylene glycol, hydroxypropylmethyl-cellulose or silica; disintegrants, such as potato starch; or lubricants, such as sodium sulfric laurate. The tablets may be coated in a well-known method in the art.

For preparation of ointment, L-carnosine powder in a sufficient amount of form the ointment of a desired concentration may be mixed with an ointment base, such as bleached wax, whale wax, dehydrated lanoline, white vaseline, higher alcohols, macrogols or plastibase (for example, ointment base of hydrocarbon gel from Taisho Pharmaceutical Co., Ltd.), hydrophilic ointment, absorptive ointment or mixture thereof, to which may be added, if desired, oils (such as sesame oil, peanut oil or olive oil), resins, glycerol, propylene glycol, surfactants, fungicides, anti-fungal agents, anti-oxidants, and others, and then kneaded homogenously.

The immuno-regulator according to the invention will be illustrated with examples below.

EXAMPLE 1

(Injectable Solution)

Synthetic L-carnosine was dissolved under an aseptic condition to prepare its 0.3%, 0.5% or 1.0% isotonic solution, which was then filled in an ampoule.

EXAMPLE 2

(Granules)

Synthetic L-carnosine was used to prepare granules of the following formulation:

| | | |
|---|---|---|
| L-carnosine | 0.2 g | |
| Lactose | 0.34 g | |
| Corn Starch | 0.45 g | |
| Hydroxypropylmethyl-cellulose | 0.01 g | |
| Granules | 1.00 g | |

EXAMPLES 3

(Ointment)

Synthetic L-carnosine and an ointment base of hydrocarbon gel were used to prepare a 1.0% ointment of the following formulation:

| | |
|---|---|
| L-carnosine | 1.0 g |
| Hydrocarbon Gel | 99.0 g |
| Ointment | 100.0 g |

What is claimed is:

1. A pharmaceutical composition for the treatment of immuno-diseases including serum disease, lupus erythematosus, various types of rheumatism, mixed clioglobulinemia, mixed connective tissue disease, HBV (hepatic virus B-type) antigen-antibody complex disease, immunoblast lymphadenitia, scleroderma, mesenchyma ataxic syndrome, serious myasthenia, Hashimoto's disease, Basedow's disease, asmyloidosis, Behcet's syndrome, immuno-insufficience syndrome, Hodgkin's disease, multiple sclerosis, and organ-specific autoimmune disease or for use in conjunction with the transplantation of organs, comprising a pharmaceutical carrier and L-carnosine or pharmaceutically acceptable salt thereof as an immuno-regulator in an amount sufficient to provide a patient suffering from said immuno-disease or who has received a transplanted organ a dosage amount of said L-carnosine or salt thereof on the order of 100 mg/kg/day, in a dosage form suitable for subcutaneous administration.

2. A method of suppressing immuno-reactions in a patient in need of such therapy, comprising administering to a patient suffering from an immuno-disease an amount sufficient of L-carnosine or pharmaceutically acceptable salt thereof to suppress an immuno-response.

3. A method according to claim 2 wherein said administering is effected by subcutaneous injection.

4. A method according to claim 3 wherein said amount is on the order of about 100 mg/kg/day.

5. A method according to claim 2 for the treatment of Behcet's syndrome wherein said administering is effected by topically applying to an affected area said L-carnosine or pharmaceutically acceptable salt thereof.

6. A method according to claim 5 wherein said L-carnosine or pharmaceutically acceptable salt thereof is used in the form of a mouth ointment.

7. A method for the treatment of cachexia in a patient in need of such therapy, comprising administering orally or by injection to a patient suffering from cachexia an amount sufficient of L-carnosine or a pharmaceutically acceptable salt thereof to reduce said cachexia.

* * * * *